United States Patent [19]

Junino et al.

[11] Patent Number: 4,865,619
[45] Date of Patent: Sep. 12, 1989

[54] USE, AS A COUPLER, OF 2,4-DIAMINO-1,3-DIMETHOXYBENZENE OR ONE OF ITS SALTS, IN COMBINATION WITH OXIDATION DYE PRECURSORS, FOR DYEING HUMAN HAIR, HAIR DYEING COMPOSITION CONTAINING THE SAID COUPLER AND PROCESS FOR PREPARING THE SAID COUPLER

[75] Inventors: Alex Junino, Livry-Gargan; Jean J. Vandenbossche, Aulnay-sous-Bois; Hervé Borowiak, Tremblay-les-Gonesse; Gérard Lang, Saint Gratien, all of France

[73] Assignee: L'Oreal, Paris, France

[21] Appl. No.: 200,163

[22] Filed: May 31, 1988

[30] Foreign Application Priority Data

May 29, 1987 [LU] Luxembourg ............................ 86903

[51] Int. Cl.$^4$ .................... A61K 7/13; C07C 91/40; C07C 91/42
[52] U.S. Cl. ................................. 8/412; 8/410; 8/411; 8/424; 564/443
[58] Field of Search .................... 564/443; 8/408, 411, 8/412, 416, 424

[56] References Cited

U.S. PATENT DOCUMENTS 4,566,876  1/1986  Brown et al. ........................... 8/411

FOREIGN PATENT DOCUMENTS 0075242  3/1983  European Pat. Off. .
2268786  11/1975  France .
2542193  9/1984  France .
2018303  10/1979  United Kingdom .

OTHER PUBLICATIONS

Handbuch der organischen Chemie, Fourth Edition, Third Supplement, vol. 13, pp. 2144–2145.
Houben–Weyl, Methoden der Organische Chemie, Fourth Ed., vol. XI/1, 1957, pp. 343–406, Glaser et al.

Primary Examiner—Paul Lieberman
Assistant Examiner—John F. McNally
Attorney, Agent, or Firm—Cushman, Darby & Cushman

[57] ABSTRACT

The invention relates to the use, by way of a coupler, of 2,4-diamino-1,3-dimethoxybenzene or one of its addition salts with an acid, in combination with at least one oxidation dye precursor of the para type, for dyeing keratinous fibres and especially human hair.

The hair dyeing compositions according to the invention contain, in a cosmetically acceptable aqueous vehicle, 0.05 to 3.5% by weight of 2,4-diamino-1,3-dimethoxybenzene or one of its salts, which imparts to the hair strong blue colorations when it is combined with p-phenylenediamines or red colorations when it is combined with p-aminophenols, in an oxidizing alkaline medium.

21 Claims, No Drawings

USE, AS A COUPLER, OF 2,4-DIAMINO-1,3-DIMETHOXYBENZENE OR ONE OF ITS SALTS, IN COMBINATION WITH OXIDATION DYE PRECURSORS, FOR DYEING HUMAN HAIR, HAIR DYEING COMPOSITION CONTAINING THE SAID COUPLER AND PROCESS FOR PREPARING THE SAID COUPLER

The present invention relates to the use, by way of a coupler, of 2,4-diamino-1,3-dimethoxybenzene or one of its salts, in combination with oxidation dye precursors, for dyeing keratinous fibres and especially human hair, to a hair-dyeing composition containing said coupler, to a dyeing process using the said composition and to a process for preparing said coupler.

It is known that it is common to use, for dyeing keratinous fibres such as human hair or furs, dyeing compositions containing oxidation dye precursors and especially para-phenylene diamines or ortho- or para-aminophenols, which are generally designated by the term oxidation bases.

It is also known that, in order to vary the hues obtained with these oxidation bases, dye modifiers or couplers, and especially meta-aminophenols, meta-diphenols and aromatic meta-phenylenediamines, are used.

In the oxidizing alkaline media normally used in oxidation dye, para-phenylenediamines and para-aminophenols give rise, in the presence of couplers such as meta-phenylenediamines, to coloured indamines or indoanilines.

The indamines formed from meta-phenylenediamines and from para-phenylenediamines in an oxidizing alkaline medium, and more especially in the presence of hydrogen peroxide, impart very strong blue colorations to keratinous fibres. The indoanilines formed from meta-phenylenediamines and from para-aminophenols in an oxidizing alkaline medium impart red colorations that are more or less purple to keratinous fibres. Depending on the oxidation bases with which they are combined, meta-phenylenediamines can hence give red or blue colorations, these being two fundamental colours in hair dyeing which are essential for obtaining not only blacks and greys, but also copper-coloured or ashen chestnut browns. The extremely important role played by meta-phenylenediamines in oxidation hair dyeing is hence apparent.

It is important, moreover, that the oxidation dye precursors and the couplers which are used in oxidation dyeing compositions impart to the hair, in an oxidizing alkaline medium, colourations which are stable to light, to washing, to inclement weather and to perspiration. It is desirable that these colorations should have little or no selectivity, that is to say that the colours obtained on natural hair and on hair sensitisized by permanent waving or bleaching should be substantially identical. It is also necessary that these compounds should enjoy the advantage of being completely harmless.

Many couplers of the type comprising meta-phenylenediamine substituted on the aromatic ring are already known. However, a large number of these do not meet the desired requirements.

The Applicant has just discovered that 2,4-diamino-1,3-dimethoxybenzene, a compound which is known per se, as well as its addition salts with an acid, meet these collective requirements and can be advantageously used as couplers in combination with other oxidation dye precursors and in particular precursors of the para type. Another advantage of this coupler is that it is nonmutagenic.

The subject of the present invention is hence the use, by way of a coupler, of 2,4-diamino-1,3-dimethoxybenzene or one of its addition salts with an acid, in combination with oxidation dye precursors, for dyeing keratinous fibres and especially human hair.

2,4-Diamino-1,3-dimethoxybenzene or one of its salts, in combination with p-phenylenediamines in an oxidizing alkaline medium, imparts to hair strong blue colorations that are more or less rich in green or purple.

When this coupler is combined with p-aminophenols in an oxidizing alkaline medium, it imparts to hair red colorations having good stability.

The subject of the present invention is hence also a hair dyeing composition comprising, in a cosmetically acceptable aqueous vehicle, 2,4-diamino-1,3-dimethoxybenzene or one of its addition salts with an acid, by way of a coupler, in combination with at least one oxidation dye precursor of the para type.

Another subject of the invention consists of a hair dyeing process employing development with an oxidizing agent, using the composition as defined above.

2,4-Diamino-1,3-dimethoxybenzene hydrochloride may be prepared according to known processes such as, for example, by reduction of 2,4-dinitro-1,3-dimethoxybenzene with a mixture of concentrated hydrochloric acid and tin. 2,4-Dinitro-1,3-dimethoxybenzene is obtained by alklyation of 2-nitroresorcinol, which leads to 2-nitro-1,3-dimethoxybenzene which is then nitrated. 2,4-Dinitro-1,3-dimethoxybenzene is thereby obtained. This process is described in more detail in BAKER, J. C. S, 2876–78 (1932).

By means of this lengthy and expensive process, 2,4-diamino-1,3-dimethoxybenzene hydrochloride having only moderate purity may be obtained.

In point of fact, the Applicant has discovered a new process for preparing 2,4-diamino-1,3-dimethoxybenzene which is very easy to carry out, and this forms another subject of the invention.

This process consists in consecutively or simultaneously reducing and dehalogenating 2,4-dimethoxy-3,5-dinitrochlorobenzene.

Process I—reduction followed by dehalogenation

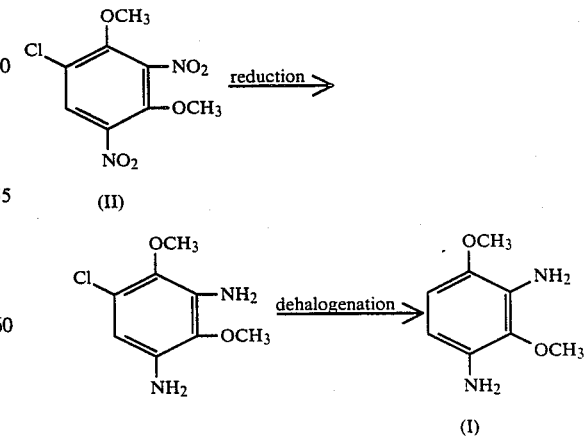

2,4-Dimethoxy-3,5-dinitrochlorobenzene is reduced with iron in the presence of acetic acid, at a temperature of between 50° and 100° C. 2,4-Dimethoxy-3,5-diaminochlorobenzene is thereby obtained, and this is then subjected to a dehalogenation reaction. This reaction is performed in water, in a lower alcohol or in an aqueous-alcoholic mixture, in the presence of palladium on charcoal, ammonium acetate and triethylamine formate, at a temperature between 50° C. and the refluxing temperature of the solvent.

Process II—simultaneous reduction and dehalogenation

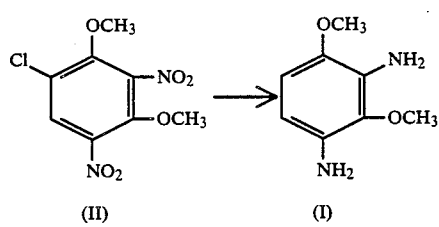

2,4-Dimethoxy-3,5-dinitrochlorobenzene is simultaneously reduced and dehalogenated under hydrogen pressure in the presence of palladium on charcoal, as described in the article "Catalytic hydrogenation", Organic Synthesis, RYLANDER, ACADEMIC PRESS Inc..

To favour the reaction, it is preferable to add ammonium acetate or triethylamine.

This reaction is performed in a solvent which can be water, lower alcohol or an aqueous-alcoholic mixture, at a temperature varying between 50° C. and 200° C.

The compound of formula (II), namely the 2,4-dimethoxy-3,5-dinitrochlorobenzene, may be obtained according to one of the following three processes:

(a) First process

This process is described in "Recueil T. Chimiques Pays-Bas", R 40, 451–471.

It consists in nitrating 1,2,4-trichlorobenzene with fuming nitric acid, optionally in the presence of $H_2SO_4$, to obtain 1,2,4-trichloro-3,5-dinitrobenzene. The chlorine atoms at the 2- and 4-positions are then substituted by a methoxy group, by the reaction of an alkali metal methylate. The process is outlined below:

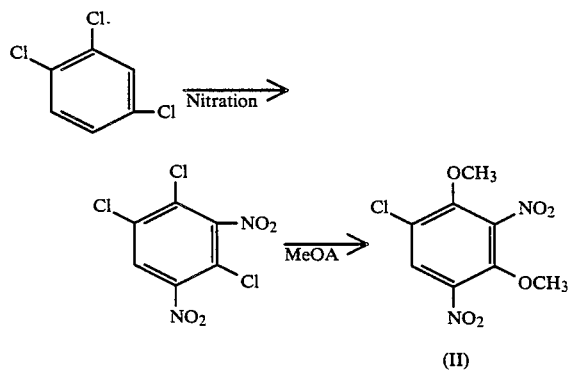

A being an alkali metal.

(b) Second Process

This consists in nitrating 2,4-dimethoxychlorobenzene with fuming nitric acid, optionally in the presence of $H_2SO_4$. 2,4-Dimethoxy-3,5-dinitrochlorobenzene is obtained in a single step. This process is outlined below:

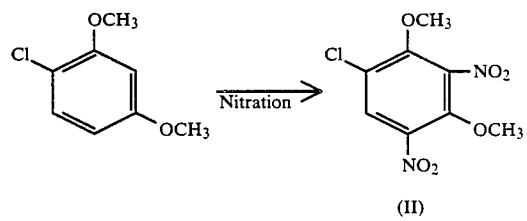

(c) Third process 3,6-Dichlorophenol or 3,4-dichlorophenol is subjected to a methylation followed by a nitration and then a substitution of the chlorine atoms by a methoxy group by the action of an alkali metal methylate. These reactions may be represented by the two schemes below:

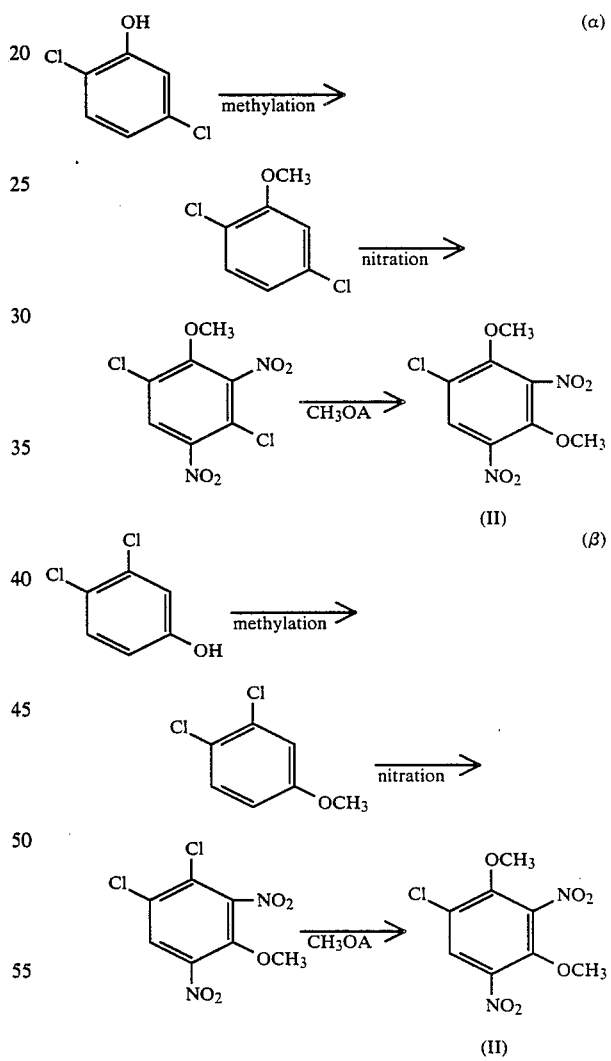

A being an alkali metal.

The oxidation hair dyeing compositions according to the invention comprise, in a cosmetically acceptable aqueous vehicle, 2,4-diamino-1,3-dimethoxybenzene or one of its addition salts with an acid, by way of a coupler, and at least one oxidation dye precursor of the para type.

The oxidation dye precursor of the para type is chosen from benzene derivatives or heterocyclic derivatives such as, for example, pyridine, to which two amino groups or an amino group and a hydroxy group are attached in the para position. These oxidation dye precursors may be present in the dye compositions in the form of free bases or in the form of addition salts with acids.

The especially preferred oxidation dye precursors which may be used according to the invention are chosen from para-phenylenediamines corresponding to the general formula (III) below:

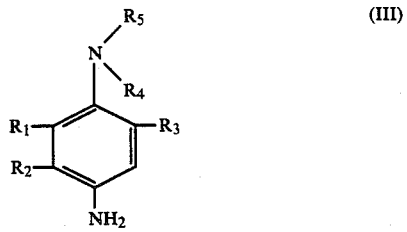

or their corresponding salts, in which formula $R_1$, $R_2$ and $R_3$ are identical or different and denote a hydrogen or halogen atom, an alkyl radical having 1 to 4 carbon atoms or an alkoxy radical having 1 to 4 carbon atoms, $R_4$ and $R_5$ are identical or different and denote a hydrogen atom, an alkyl, hydroxyalkyl, alkoxyalkyl, carbamylalkyl, mesylaminoalkyl, acetylaminoalkyl, ureidoalkyl, carbethoxyaminoalkyl, piperidinoalkyl or morpholinoalkyl radical, the alkyl or alkoxy groups denoted by $R_4$, $R_5$ having from 1 to 4 carbon atoms, or alternatively $R_4$ and $R_5$ can form, together with the nitrogen atom to which they are attached, a piperidino or morpholino heterocycle, with the proviso that $R_1$ or $R_3$ denotes a hydrogen atom when $R_4$ and $R_5$ do not denote a hydrogen atom.

Among the compounds of formula (III), there may be mentioned p-phenylenediamine, p-tolylenediamine, methoxy-para-phenylenediamine, chloro-para-phenylenediamine, 2,6-dimethyl-p-phenylenediamine, 2,5-dimethyl-para-phenylenediamine, 2,3-dimethyl-p-phenylenediamine, isopropyl-p-phenylenediamine, 2-methyl-5-methoxy-para-phenylenediamine, 2,6-dimethyl-5-methoxy-para-phenylenediamine, N,N-dimethyl-para-phenylenediamine, 3-methyl-4-amino-N,N-diethylaniline, N,N-bis(β-hydroxyethyl)-para-phenylenediamine, 3-methyl-4-amino-N,N-bis(β-hydroxyethyl)aniline, 3-chloro-4-amino-N,N-bis(β-hydroxyethyl)-aniline, 4-amino-N-ethyl-N-(carbamylmethyl)aniline, 3-methyl-4-amino-N-ethyl-N-(carbamylmethyl)aniline, 4-amino-N-ethyl-N-(β-piperidinoethyl)aniline, 3-methyl-4-amino-N-ethyl-N-(β-piperidinoethyl)aniline, 4-amino-N-ethyl-N-(β-morpholinoethyl)aniline, 3-methyl-4-amino-N-ethyl-N-(β-morpholinoethyl)aniline, 4-amino-N-ethyl-N-(β-acetylaminoethyl)aniline, 4-amino-N-(β-methoxyethyl)aniline, 3-methyl-4-amino-N-ethyl-N-(β-acetylaminoethyl)aniline, 4-amino-N-ethyl-N-(β-mesylaminoethyl)aniline, 3-methyl-4-amino-N-ethyl-N-(β-mesylaminoethyl)aniline, 4-amino-N-ethyl-N-(β-sulphoethyl)aniline, 3-methyl-4-amino-N-ethyl-N-(β-sulphoethyl)aniline, N-(4-aminophenyl)morpholine and N-(4-aminophenyl)-piperidine. These oxidation dye precursors of the para type may be introduced into the dyeing composition in the form of the free base or in the form of salts, such as in the form of the hydrochloride, hydrobromide or sulphate.

2,4-Diamino-1,3-dimethoxybenzene or its salts can also be used as para-aminophenols to give hues which are especially stable to light, to inclement weather and to washing, after development in the presence of an oxidizing agent. Among para-aminophenols, there may be mentioned p-aminophenol, 2-methyl-4-aminophenol, 3-methyl-4-aminophenol, 2-chloro-4-aminophenol, 3-chloro-4-aminophenol, 2,6-dimethyl-4-aminophenol, 3,5-dimethyl-4-aminophenol, 2,3-dimethyl-4-aminophenol, 2,5-dimethyl-4-aminophenol, 2-hydroxymethyl-4-aminophenol, 2-(β-hydroxyethyl)-4-aminophenol, 2-methoxy-4-aminophenol and 3-methoxy-4-aminophenol.

2,4-Diamino-1,3-dimethoxybenzene or its salts can also be used with heterocyclic para oxidation dye precursors, among which 2,5-diaminopyridine, 2-hydroxy-5-aminopyridine and tetraaminopyrimidine may be mentioned.

The dyeing compositions according to the invention can also contain oxidation dye precursors of the ortho type, such as ortho-aminophenols, ortho-phenylenediamines and ortho-diphenols. 1-Amino-2-hydroxybenzene, 6-methyl-1-hydroxy-2-aminobenzene and 4-methyl-1-amino-2-hydroxybenzene may be mentioned, for example.

The dyeing compositions according to the invention containing 2,4-diamino-1,3-dimethoxybenzene or its salts can optionally contain other couplers which are known per se, such as meta-diphenols, meta-aminophenols, meta-phenylenediamines, meta-acylaminophenols, meta-ureidophenols, meta-carbalkoxyaminophenols, α-naphthol, and couplers possessing an active methylene group such as β-keto compounds and pyrazolones.

There may be mentioned, in particular, by way of example, 2,4-dihydroxyphenoxyethanol, 2,4-dihydroxyanisole, meta-aminophenol, resorcinol, resorcinol monomethyl ether, 2-methyl-5-aminophenol, 2-methyl-5-[N-(β-hydroxyethyl)amino]phenol, 2-methyl-5-[N-(β-mesylaminoethyl)amino]phenol, 2,6-dimethyl-3-aminophenol, 6-hydroxybenzomorpholine, 2,4-diaminophenoxyethanol, 6-aminobenzomorpholine, 2-[N-(β-hydroxyethyl)amino]-4-aminophenoxyethanol, 2-amino-4-[N-(β-hydroxyethyl)amino]-anisole, 2,4-diaminophenyl β,γ-dihydroxypropyl ether, 2,4-diaminophenoxyethylamine, 3,4-methylenedioxyphenol and 3,4-methylenedioxyaniline, and the salts thereof.

As is well known, it is possible to add to these compositions, for the purpose of altering the hue or enriching in glints the colorations provided by the oxidation dye precursors, direct dyes such as azo or anthraquinone dyes, or nitro derivatives of the benzene series.

The para compounds and the couplers used in the dyeing compositions according to the invention preferably represent collectively from 0.1 to 7% of the total weight of the said compositions. The concentration of 2,4-diamino-1,3-dimethoxybenzene can vary between 0.05 and 3.5% of the total weight of the composition.

The cosmetically acceptable aqueous vehicle has a pH which can vary between 8 and 11; it is preferably between 9 and 11.

It is adjusted to the desired value using an alkalinizing agent such as ammonia solution, alkali metal carbonates or alkanolamines such as mono-, di- or triethanolamine.

The dyeing compositions according to the invention also contain, in their preferred embodiment, anionic, cationic, nonionic or amphoteric surfactants, or mixtures thereof. Among these surfactants, there may be mentioned, more especially, alkylbenzenesulphonates, alkylnaphthalenesulphonates, fatty alcohols, sulphates, fatty alcohol ether sulphates and fatty alcohol sulphonates, quaternary ammonium salts such as trimethylcetylammonium bromide and cetylpyridinium bromide, fatty acid ethanolamides, optionally oxyethylenated, polyoxyethylenated acids, alcohols and amines polyglycerolated alcohols, polyoxyethylenated or polyglycerolated alkylphenols and also polyoxyethylenated alkyl sulphates. The surfactants are present in the compositions according to the invention in proportions of between 0.5 and 40% by weight and preferably between 4 and 30% by weight, based on the total weight of the compositions.

These compositions can also contain organic solvents for solubilizing compounds which are insufficiently soluble in water. Among these solvents, there may be mentioned, by way of example, $C_1$–$C_4$ lower alkanols such as ethanol and isopropanol; glycerol; glycols or glycol ethers such as 2-butoxyethanol, ethylene glycol, propylene glycol, diethylene glycol monoethyl ether and monomethyl ether; as well as similar products and mixtures thereof. Solvents are preferably present in a proportion of between 1 and 40% by weight, and especially between 5 and 30% by weight, based on the total weight of the composition.

Thickening agents which may be added to the compositions according to the invention are selected, in particular, from the group composed of sodium alginate, gum arabic, cellulose derivatives such as methylcellulose, hydroxyethylcellulose, hydroxypropylcellulose, hydroxymethylcellulose and carboxymethylcellulose, acrylic acid polymers and xanthan gum. It is also possible to use inorganic thickening agents such as bentonite. These thickening agents are preferably present in proportions of between 0.1 and 5% by weight, and especially between 0.5 and 3% by weight, based on the total weight of the composition.

The compositions can contain antioxidant agents chosen, in particular, from sodium sulphite, thioglycolic acid, sodium bisulphite, ascorbic acid and hydroquinone. These antioxidation agents are present in the composition in proportions of between 0.05 and 1.5% by weight, based on the total weight of the composition.

Other adjuvants which are usable according to the invention are, for example, penetrating agents, sequestering agents, buffers and perfumes.

The dyeing compositions according to the invention may be presented in various forms, such as in the form of liquids, creams or gels, or in any other form suitable for carrying out the dyeing of keratinous fibres, and especially human hair. They can also be packaged in aerosol cans in the presence of a propellant.

The dyeing compositions according to the invention, containing an oxidation dye precursor of the para type and 2,4-diamino-1,3-dimethoxybenzene or one of its salts, are used in a hair dyeing process employing development with an oxidizing agent.

According to this process, the dyeing composition described above is mixed at the time of use with a sufficient quantity of an oxidizing solution, and the mixture obtained is then applied on the hair.

The oxidizing solution contains oxidizing agents such as hydrogen peroxide, urea peroxide or persalts such as ammonium persulphate. "20 volumes" hydrogen peroxide solution is preferably used.

The mixture obtained is applied on the hair; it is left in place for 10 to 40 minutes, preferably 15 to 30 minutes, after which the hair is rinsed, washed with shampoo, rinsed again and dried.

Another process for employing 2,4-diamino-1,3-dimethoxybenzene according to the invention consists in dyeing the hair on the basis of a multi-stage process, according to which, in a first stage, the oxidation dye precursor of the para type is applied by means of a composition defined above and, in a second stage, the 2,4-diamino-1,3-dimethoxybenzene is applied. The oxidizing agent is present in the composition applied in the second stage, or is alternatively applied on the hair itself in a third stage, the conditions of exposure, drying and washing being identical to those stated in the above process.

The examples below serve to give a better illustration of the invention, but under no circumstances limit the scope of the latter.

PREPARATION EXAMPLE NO. 1: PROCESS I

First stage: Reduction

Preparation of 2,4-dimethoxy-3,5-diaminochlorobenzene dihydrochloride

To 270 ml of water to which 27 ml of acetic acid have been added, heated beforehand to 80° C., there are added 100 g of powdered iron reduced with hydrogen and, in small portions and with stirring, 0.25 mole (66 g) of 2,4-dimethoxy-3,5-dinitrochlorobenzene. When the additions are complete, the reaction medium is maintained on a boiling water bath for a further 30 minutes. After being cooled, the reaction medium is centrifuged. The ferric sludge which contains the expected product is taken up with acetone using stirring. After filtration of the ferric sludge followed by washing with acetone, the expected product precipitates from the acetone filtrate on addition of a solution of hydrochloric acid in ethanol. After filtration with suction and washing, the expected product is recrystallized hot from a mixture of hydrochloric acid and water.

The elemental analysis of the product obtained gives the following results:

| Analysis | Calculated for $C_8H_{13}N_2Cl_3O_2$ | Found |
| --- | --- | --- |
| C% | 34.85 | 34.85 |
| H% | 4.72 | 4.82 |
| N% | 10.16 | 10.03 |
| O% | 11.62 | 11.80 |
| Cl% | 38.65 | 38.46 |

Second stage: Dehalogenation

Preparation of 2,4-diamino-1,3-dimethoxybenzene dihydrochloride

A mixture consisting of 77 g of ammonium acetate, 42 g of palladium on charcoal (10% palladium) and 0.25 mole (69 g) of 2,4-dimethoxy-3,5-diaminochlorobenzene dihydrochloride in 420 ml of ethanol to which 50 ml of water have been added is heated to 75° C. with stirring. 75 g of triethylamine are added, followed, dropwise, by 31 g of formic acid. After a further 30 minutes' heating, the reaction medium is filtered hot. The filtrate is evaporated to dryness. On addition of ethyl acetate, the inorganic salts are precipitated, and these are removed by filtration with suction. To the filtrate, dried over sodium sulphate, 100 ml of a 7N alcoholic solution of hydrochloric acid are added. The expected product precipitates, and is recrystallized from a mixture of water and a solution of hydrochloric acid in ethanol.

The elemental analysis of the product obtained gives the following results:

| Analysis | Calculated for $C_8H_{14}N_2O_2Cl_2$ | Found |
|---|---|---|
| C% | 39.83 | 39.75 |
| H% | 5.81 | 5.79 |
| N% | 11.62 | 11.60 |
| O% | 13.28 | 13.54 |
| Cl% | 29.46 | 29.29 |

PREPARATION EXAMPLE NO. 2: PROCESS II

Preparation of 2,4-diamino-1,3-dimethoxybenzene dihydrochloride (directly from 2,4-dimethoxy-3,5-dinitrochlorobenzene)

A mixture consisting of 0.1 mole (26.2 g) of 2,4-dimethoxy-3,5-dinitrochlorobenzene, 15.4 g of ammonium acetate and 5.2 g of palladium on charcoal (10% palladium) in 100 ml of ethanol to which 15 ml of water have been added is heated to 80° C. for 1 hour under a hydrogen pressure of 20 kg.

The reaction medium is filtered hot in order to remove the catalyst. The filtrate is evaporated to dryness under reduced pressure. Ethyl acetate is added to the filtrate in order to precipitate the inorganic salts, which are removed by filtration. The filtrate is dried over sodium sulphate. The expected product precipitates on addition of 43 ml of a 7N solution of hydrochloric acid in absolute ethanol. It is identical to the product prepared in Preparation Example No. 1.

DYEING EXAMPLE 1

The following dyeing mixture is prepared:

| | |
|---|---|
| 2,4-Diamino-1,3-dimethoxybenzene dihydrochloride | 0.602 g |
| p-Phenylenediamine | 0.27 g |
| Oleyl alcohol polyglycerolated with 2 moles of glycerol | 4.5 g |
| Oleyl alcohol polyglycerolated with 4 moles of glycerol | 4.5 g |
| ETHOMEEN O 12 - company ARMOON HESS CHEMICAL Ltd (oleylamine oxyethylenated with 12 moles of E.O.) | 4.5 g |
| COMPERLAN KD - company HENKEL (coconut diethanolamide) | 9 g |
| Propylene glycol | 4 g |
| 2-Butoxyethanol | 8 g |
| Ethanol, 96° strength | 6 g |
| MASQUOL DTPA - company PROTEX (pentasodium salt of diethylenetriaminepentaacetic acid) | 2 g |
| Hydroquinone | 0.15 g |
| Sodium bisulphite solution, 35° Be | 1.3 g |
| Ammonia solution 22° Be | 10 g |
| Water qs | 100 g |
| pH:10 | |

At the time of use, 100 g of "20 volumes" hydrogen peroxide are added. When applied for 20 minutes at 30° C. on permanent-waved hair, the mixture imparts to it, after shampooing and rinsing, a deep greyish blue coloration.

DYEING EXAMPLE 2

The following dyeing composition is prepared:

| | |
|---|---|
| 2,4-Diamino-1,3-dimethoxybenzene dihydrochloride | 0.602 g |
| p-Aminophenol | 0.275 g |
| Oleyl alcohol polyglycerolated with 2 moles of glycerol | 4.5 g |
| Oleyl alcohol polyglycerolated with 4 moles of glycerol | 4.5 g |
| ETHOMEEN O 12 - company ARMOON HESS CHEMICAL Ltd (oleylamine oxyethylenated with 12 moles of E.O.) | 4.5 g |
| COMPERLAN KD - company HENKEL (coconut diethanolamide) | 9 g |
| Propylene glycol | 4 g |
| 2-Butoxyethanol | 8 g |
| Ethanol, 96° strength | 6 g |
| MASQUOL DTPA - company PROTEX (pentasodium salt of diethylenetriaminepentaacetic acid) | 2 g |
| Hydroquinone | 0.15 g |
| Sodium bisulphite solution, 35° Be | 1.3 g |
| Ammonia solution 22° Be | 10 g |
| Water qs | 100 g |
| pH: 10 | |

At the time of use, 100 g of "20 volumes" hydrogen peroxide are added. When applied for 20 minutes at 30° C. on bleached hair the mixture imparts to it, after shampooing and rinsing, a greyish purple-red coloration.

DYEING EXAMPLE 3

The following dyeing mixture is prepared:

| | |
|---|---|
| 2,4-Diamino-1,3-dimethoxybenzene dihydrochloride | 0.602 g |
| 4-Amino-N—[β-methoxyethyl]aniline dihydrochloride | 0.598 g |
| CEMULSOL NP 4 - RHONE POULENC (nonylphenol oxyethylenated with 4 moles E.D.) | 12 g |
| CEMULSOL NP 9 - RHONE POULENC (nonylphenol oxyethylenated with 9 moles E.O.) | 15 g |
| Oleyl alcohol polyglycerolated with 2 moles of glycerol | 1.5 g |
| Oleyl alcohol polyglycerolated with 4 moles of glycerol | 1.5 g |
| Propylene glycol | 6 g |
| TRILON B (ethylenediaminetetraacetic acid) | 0.12 g |
| Ammonia 22° Be | 11 g |
| Thioglycolic acid | 0.6 g |
| Water qs | 100 g |
| pH: 10.5 | |

At the time of use, 100 g of "20 volumes" hydrogen peroxide are added. When applied for 20 minutes at 35° C. on bleached hair, the mixture imparts to it, after shampooing and rinsing, a deep blue coloration.

DYEING EXAMPLE 4

The following dyeing composition is prepared:

| | |
|---|---|
| 2,4-Diamino-1,3-dimethoxybenzene dihydrochloride | 0.602 g |
| 2-Methyl-4-Aminophenol | 0.31 g |
| CEMULSOL NP 4 - RHONE POULENC (nonylphenol oxyethylenated with 4 moles E.O.) | 12 g |
| CEMULSOL NP 9 - RHONE POULENC (nonylphenol oxyethylenated with 9 moles E.O.) | 15 g |
| Oleyl alcohol polyglycerolated with 2 moles of glycerol | 1.5 g |
| Oleyl alcohol polyglycerolated with 4 moles of glycerol | 1.5 g |
| Propylene glycol | 6 g |
| TRILON B (ethylenediaminetetraacetic acid) | 0.12 g |
| Ammonia 22° Be | 11 g |
| Water qs | 100 g |
| pH: 10.0 | |

At the time of use, 100 g of "20 volumes" hydrogen peroxide are added. When applied for 25 minutes at 35° C. on bleached hair, the mixture imparts to it, after shampooing and rinsing, a greyish purple-red coloration.

DYEING EXAMPLE 5

The following dyeing mixture is prepared:

| | |
|---|---|
| 2,4-Diamino-1,3-dimethoxybenzene dihydrochloride | 0.602 g |
| p-Tolylenediamine dihydrochloride | 0.49 g |
| ALFOL C 16/18 - company CONDEA (cetyl/stearyl alcohol) | 8 g |
| CIRE DE LANETTE E - company HENKEL (sodium cetyl/stearyl sulphate) | 0.5 g |
| CEMULSOL B - RHONE POULENC (ethoxylated castor oil) | 1 g |
| Oleic diethanolamide | 1.5 g |
| MASQUOL DTPA - company PROTEX (pentasodium salt of diethylene triamine pentaacetic acid) | 2.5 g |
| Ammonia solution 22° Be | 11 g |
| Water qs | 100 g |
| pH: 10 | |

At the time of use, 100 g of "20 volumes" hydrogen peroxide are added. When applied for 25 minutes at 35° C. on natural hair, the mixture imparts to it, after shampooing and rinsing, a deep purple-blue coloration.

DYEING EXAMPLE 6

The following dyeing mixture is prepared:

| | |
|---|---|
| 2,4-Diamino-1,3-dimethoxybenzene dihydrochloride | 0.089 g |
| para-Phenylenediamine | 0.134 g |
| para-Aminophenol | 0.16 g |
| Resorcinol | 0.13 g |
| meta-Aminophenol | 0.09 g |
| 2-Methyl-5-[N—(β-hydroxyethyl)amino]phenol | 0.1 g |
| CEMULSOL NP 4 - RHONE POULENC (nonylphenol oxyethylenated with 4 moles E.O.) | 12 g |
| CEMULSOL NP9 - RHONE POULENC (nonylphenol oxyethylenated with 9 moles E.O.) | 15 g |
| Oleyl alcohol polyglycerolated with 2 moles of glycerol | 1.5 g |
| Oleyl alcohol polyglycerolated with 4 moles of glycerol | 1.5 g |
| Propylene glycol | 6 g |
| TRILON B (ethylenediaminetetraacetic acid) | 0.12 g |
| Ammonium solution, 22° Be | 11 g |
| Water qs | 100 g |
| pH: 8.6 | |

At the time of use, 100 g of "20 volumes" hydrogen peroxide are added. When applied for 25 minutes at 35° C. on permanent-waved hair, the mixture imparts to it, after shampooing and rinsing, a deep purple-grey coloration.

DYEING EXAMPLE 7

The following dyeing mixture is prepared:

| | |
|---|---|
| 2,4-Diamino-1,3-dimethoxybenzene dihydrochloride | 1.2 g |
| N,N—bis(β-Hydroxyethyl)-para-phenylenediamine dihydrochloride | 1.34 g |
| ALFOL C 16/18 - company CONDEA (cetyl/stearyl alcohol) | 8 g |
| CIRE DE LANETTE E - company HENKEL (sodium cetyl/stearyl sulphate) | 0.5 g |
| CEMULSOL B - RHONE POULENC (ethoxylated castor oil) | 1 g |
| Oleic diethanolamide | 1.5 g |
| MASQUOL DTPA - company PROTEX (pentasodium salt of diethylene triamine pentaacetic acid) | 2.5 g |
| Ammonia solution 22° Be | 11 g |
| Water qs | 100 g |
| pH: 9.9 | |

At the time of use, 100 g of "20 volumes" hydrogen peroxide are added. When applied for 15 minutes at 35° C. on hair which is naturally 90% white, the mixture imparts to it, after shampooing and rinsing, a Thames blue coloration.

DYEING EXAMPLE 8

The following dyeing mixture is prepared:

| | |
|---|---|
| 2,4-Diamino-1,3-dimethoxybenzene dihydrochloride | 1.2 g |
| Isopropyl-p-phenylenediamine dihydrochloride | 1.1 g |
| CARBOPOL 934 - company GOODRICH CHEMICALS | 3 g |
| Alcohol, 96° strength | 11 g |
| 2-Butoxyethanol | 5 g |
| Trimethylcetylammonium bromide | 2 g |
| TRILON B (ethylenediaminetetraacetic acid) | 0.2 g |
| Ammonia solution, 22° B | 10 g |
| Sodium bisulphite, 35° Be | 1 g |
| Water qs | 100 g | pH: 9

At the time of use, 100 g of "20 volumes" hydrogen peroxide are added. When applied for 25 minutes at 35° C. on hair which is naturally 90% white, the mixture imparts to it, after shampooing and rinsing, a navy blue coloration.

We claim:

1. A hair dyeing composition, which contains, in a cosmetically acceptable aqueous vehicle, 2,4-diamino-1,3-dimethoxybenzene or acid addition salts, in combination with at least one oxidation dye precursor of the para type.

2. The dye composition according to claim 1, which contans 0.05 to 3.5% by weight of 2,4-diamino-1,3-dimethoxybenzene or acid addition salts, based on the total weight of the composition.

3. The dye composition according to claim 1, wherein the oxidation dye precursor of the para type is selected from the group consisting of para-phenylenediamines, para-aminophenols, heterocyclic para compounds and mixtures thereof.

4. The dye composition according to claim 3, wherein the para-phenylenediamines correspond to the formula:

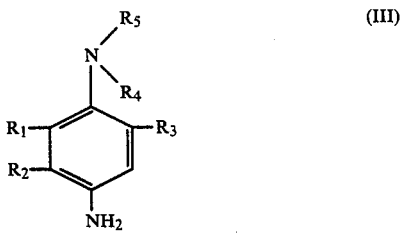

in which formula $R_1$, $R_2$ and $R_3$ are identical or different and denote a hydrogen or halogen atom, an alkyl radical having 1 to 4 carbon atoms or an alkoxy radical having 1 to 4 carbon atoms, $R_4$ and $R_5$ are identical or different and denote a hydrogen atom, an alkyl, hydroxyalkyl, alkoxyalkyl, carbamylalkyl, mesylaminoalkyl, acetylaminoalkyl, ureidoalkyl, carbethoxyaminoalkyl, piperidinoalkyl or morpholinoalkyl radical, the alkyl or alkoxy groups denoted by $R_4$, $R_5$ having from 1 to 4 carbon atoms, or alternatively $R_4$ and $R_5$ can form, together with the nitrogen atom to which they are attached, a piperidino or morpholino heterocycle, with the proviso that $R_1$ or $R_3$ denotes a hydrogen atom when $R_4$ and $R_5$ do not denote a hydrogen atom; or consist of the salts of the compounds of formula (III) above.

5. The dye composition according to claim 4 which contains at least one para-phenylenediamine selected from the group consisting of p-phenylenediamine, p-tolylenediamine, methoxy-para-phenylenediamine, chloro-para-phenylene-diamine, 2,6-dimethyl-p-phenylenediamine, 2,5-dimethyl-para-phenylenediamine, 2,3-dimethyl-p-phenylenediamine, isopropyl-p-phenylenediamine, 2-methyl-5-methoxy-para-phenylenediamine, 2,6-dimethyl-5-methoxy-para-phenylene-diamine, N,N-dimethyl-para-phenylenediamine, 3-methyl-4-amino-N,N-diethylaniline, N,N-bis(β-hydroxyethyl)-para-phenylenediamine, 3-methyl-4-amino-N,N-bis(β-hydroxy-ethyl)aniline, 3-chloro-4-amino-N,N-bis(β-hydroxyethyl)-aniline, 4-amino-N-ethyl-N-(carbamylmethyl)aniline, 3-methyl-4-amino-N-ethyl-N-(carbamylmethyl)aniline, 4-amino-N-ethyl-N-(β-piperidinoethyl)aniline, 3-methyl-4-amino-N-ethyl-N-(β-piperidinoethyl)aniline, 4-amino-N-ethyl-N-(β-morpholinoethyl)aniline, 3-methyl-4-amino-N-ethyl-N-(β-morpholinoethyl)aniline, 4-amino-N-ethyl-N-(β-acetylaminoethyl)aniline, 4-amino-N-(β-methoxyethyl)-aniline, 3-methyl-4-amino-N-ethyl-N-(β-acetylaminoethyl)-aniline, 4-amino-N-ethyl-N-(β-mesylaminoethyl)aniline, 3-methyl-4-amino-N-ethyl-N-(β-mesylaminoethyl)aniline, 4-amino-N-ethyl-N-(β-sulphoethyl)aniline, 3-methyl-4-amino-N-ethyl-N-(β-sulphoethyl)aniline, N-(4-aminophenyl)morpholine and N-(4-aminophenyl)piperidine, in the form of the free base or in the form of a cosmetically acceptable salt.

6. The dye composition according to claim 3, which contains at least one para-aminophenol selected from the group consisting of p-aminophenol, 2-methyl-4-aminophenol, 3-methyl-4-aminophenol, 2-chloro-4-aminophenol, 3-chloro-4-aminophenol, 2,6-dimethyl-4-aminophenol, 3,5-dimethyl-4-aminophenol, 2,3-dimethyl-4-aminophenol, 2,5-dimethyl-4-aminophenol, 2-hydroxymethyl-4-aminophenol, 2-(β-hydroxyethyl)-4-aminophenol, 2-methoxy-4-aminophenol and 3-methoxy-4-aminophenol.

7. The dye composition according to claim 3, wherein the oxidation dye precursor of the para type is a heterocyclic para compound selected from the group consisting of 2,5-diaminopyridine, 2-hydroxy-5-aminopyridine and tetra-aminopyrimidine.

8. The dye composition according to claim 1, which contains other couplers selected from the group consisting of meta-diphenols, meta-aminophenols, meta-phenylenediamines, meta-acylaminophenols, meta-ureidophenols, meta-carbalkoxyaminophenols, α-naphthol, β-keto compounds and pyrazolones.

9. The dye composition according to claim 1 wherein the total concentration of couplers and of oxidation dye precursors of the para type is between 0.1 and 7% by weight.

10. The dye composition according to claim 1 which contains, in addition, dye precursors of the ortho type, selected from ortho-aminophenols, ortho-phenylenediamines and orthodiphenols.

11. The dye composition according to claim 1, which contains, in addition, direct dyes chosen from the group consisting of azo and anthraquinone dyes and nitro derivatives of the benzene series.

12. The dye composition according to claim 1 which has a pH of between 8 and 11, and preferably between 9 and 11.

13. The dye composition according to claim 1 which contains 1 to 40% by weight of an organic solvent chosen from the group consisting of lower alkanols, glycerol, glycols, glycol ethers, and mixtures thereof.

14. The dye composition according to claim 1 which it contains, in addition, 0.5 to 40% by weight of at least one anionic, cationic, nonionic or amphoteric surfactant or mixtures thereof.

15. The dye composition according to claim 1 which contains, in addition, cosmetic adjuvants chosen from the group consisting of thickeners, antioxidation agents, penetrating agents, sequestering agents, buffers, perfumes, alkalinizing agents and propellants.

16. A process for preparing 2,4-diamino-1,3-dimethoxybenzene or one of its addition salts with an acid, which consists in performing the consecutive or simultaneous reduction and dehalogenation of 2,4-dimethoxy, 3,5-dinitrochlorobenzene.

17. A process for preparing 2,4-diamino-1,3-dimethoxybenzene or its addition salts with an acid according to claim 16, which consists, in the first stage, in reducing 2,4-dimethoxy-3,5-dinitrochlorobenzene with iron in the presence of acetic acid at a temperature of between 50° and 100° C., and then, in a second stage, in dehalogenating the compound thereby obtained, the second stage being performed in water, in a lower alcohol, in an aqueous-alcoholic mixture, in the presence of palladium on charcoal, ammonium acetate and triethylamine formate, at a temperature between 50° C. and the refluxing temperature of the solvent.

18. A process for preparing 2,4-diamino-1,3-dimethoxybenzene or one of its addition salts with an acid according to claim 16, which consists in simultaneously reducing and dehalogenating 2,4-dimethoxy-3,5-dinitrochlorobenzene under hydrogen pressure in the presence of palladium on charcoal, in a solvent chosen from the group consisting of water, lower alcohols, and aqueous alcoholic mixtures at a temperature of between 50° C. and 200° C. and preferably in the presence of ammonium acetate or triethylamine.

19. A process for dyeing keratinous fibers comprising contacting the keratinous fibers with an effective amount of the hair dye composition of claim 1.

20. A process for dyeing hair comprising the steps of
(a) mixing a dyeing composition according to claim 1 with an effective amount of an oxidizing solution;
(b) applying to the hair the mixture of step (a);
(c) permitting said mixture to remain in contact with the hair for a period of about 10 to 40 minutes; then
(d) rinsing;
(e) shampooing; and
(f) drying the dyed hair.

21. The process for dyeing hair comprising in sequence the steps of
(a) applying to the hair a dyeing composition containing at least one oxidation dye precursor of claim 4;
(b) applying to the hair a dyeing composition containing 2,4-diamino-1,3-dimethoxybenzene or acid salts thereof in admixture with an oxidizing agent;
(c) permitting said compositions from steps (a) and (b) to remain in contact with the hair for a period of about 10 to 40 minutes;
(d) rinsing;
(f) shampooing; and
(g) drying the dyed hair.

* * * * *